(12) United States Patent
Iimura

(10) Patent No.: US 6,239,442 B1
(45) Date of Patent: May 29, 2001

(54) CLEANING APPARATUS USING ULTRAVIOLET RAYS

(76) Inventor: Keiji Iimura, 10-8, Akatsuka 3-Chome, Itabashi-ku, Tokyo 175-0092 (JP)

( * ) Notice: Subject to any disclaimer, the term of this patent is extended or adjusted under 35 U.S.C. 154(b) by 0 days.

(21) Appl. No.: 09/161,012

(22) Filed: Sep. 25, 1998

(30) Foreign Application Priority Data

Mar. 21, 1996 (JP) .................................................... 8-103131

(51) Int. Cl.[7] .......................................................... G01J 1/00
(52) U.S. Cl. ............................... 250/504 R; 250/453.1
(58) Field of Search .......................... 250/504 H, 504 R, 250/453.1

(56) References Cited

U.S. PATENT DOCUMENTS 3,261,978 * 7/1966 Brenman ........................... 250/504 H
5,030,093 * 7/1991 Mitnick ............................. 250/504 H

FOREIGN PATENT DOCUMENTS

4206190 * 5/1993 (DE) .
09253595 * 9/1997 (JP) .

\* cited by examiner

Primary Examiner—Bruce C. Anderson

(57) ABSTRACT

Cleaning apparatus using ultraviolet rays comprises a cleaning head having a transparent body, a light source and a light guide member. capable of transmitting said ultraviolet rays from said light source to said transparent body. The transparent body is capable of transmitting ultraviolet rays. The light source is capable of emitting the ultraviolet rays. The light guide member is capable of transmitting the ultraviolet rays from the light source to the transparent body. The cleaning head may have preferably the transparent body and a group of brushes in which the group of brushes are supported by the transparent body. The cleaning apparatus may be applied for a vacuum cleaner.

20 Claims, 10 Drawing Sheets

CLEANING APPARATUS USING ULTRAVIOLET RAYS

BACKGROUND OF INVENTION

1. Technical Field

The invention relates to a cleaning apparatus for cleaning a substance or a surface of the substance.

2. Description of Prior Art

For cleaning the substance or the surface of the substance, various cleaning apparatuses or cleaning tools are used such as cleaning tool with brushes, vacuum cleaner and mop, according to the substance to be cleaned. The substance to be cleaned, includes a floor, a wall, a tile, a carpet, a bathtub, a sink, cooking utensils and a toilet pot in a house or a building.

In case the substance is a mouth cavity, they brush a surface of teeth, gums and between teeth and gums, in order to clean by using toothbrush and toothpaste.

Dirty component contacted or sticked on the substance to be cleaned (hereinafter called as cleaned substance) includes bust of textile fibers, garbage of foods, nicotine and tar of cigarettes, bacteria, molds, small animals such as flea and tic etc. When the bacteria and molds are sticked on such organic dirty components as the garbage of foods and a dead body of small animal, they increases rapidly and the cleaned substances become dirty more and more according to a lapse of time.

In the dirty components contacted or sticked inside the mouth cavity, there are a plaque, a bacteria and scale. The plaque is a harmful substance that forms on the teeth causing from the bacteria glowing themselves by taking nutriment of the foods garbage and water. The bacteria live in the plaque. The scale is Ca-phosphate caused by combining the plaque and Ca melting in saliva.

However, it is difficult to remove the dirty components such as bacteria and molds only by using the conventional cleaning apparatus or tool. Therefore it is necessary to use a cleaning agent such as soap or a sterilizing agent such as alcohol or cresol, in addition to the conventional cleaning apparatus or tool.

Since plaque is highly adhesive and is not soluble in water, it is necessary to remove the plaque from the teeth by ordinary tooth brushing. And the teeth are easy to become decayed teeth in which enamel of the teeth is dissolved by the plaque. Accordingly, they must go to a dental clinic periodically in order to remove or delete the scale, where the scale fixed on the teeth is physically remove from the teeth by use of special dental tools.

It is well known that short wave length, that is, ultraviolet (hereinafter called as "UV") light rays are able to sterilize the dirty components such as bacteria and molds by radiation of the UV light rays. The UV light rays are an invisible electromagnetic wave within a range from 380 nano meter (nm) or 3800 angstrom (Å) near visible light rays to X rays.

A conventional germicidal lamp emits or generates the UV light rays near wavelength of 260 nano meter (2600 angstrom), or wavelength between 250 nano meter (2500 angstrom) and 260 nano meter (2600 angstrom), whose wavelength of rays exhibits strong germicidal effect to the dirty component.

SUMMARY OF THE INVENTION

It is an object of the present invention is to provide novel cleaning apparatus using ultraviolet rays.

Another object of the present invention is to provide novel vacuum cleaner using ultraviolet rays.

A further object of the present invention is to provide the cleaning apparatus using ultraviolet rays, in which any chemical agents such as cleaning agent and/or sterilizing agent may not be required, in order to sterilize, dissolve and/or remove the dirty components including bacteria and/or molds, contacted or sticked on the surface of any substances.

Still a further object of the present invention is to provide the vacuum cleaner using ultraviolet rays, in which any chemical agents such as cleaning agent and/or sterilizing agent may not be required, in order to sterilize, dissolve and/or remove the dirty components including bacteria and/or molds, contacted or sticked on the surface of any substances.

To accomplish the object of the present invention, the cleaning apparatus using ultraviolet rays may comprises a cleaning head which has a transparent body capable of transmitting the ultraviolet rays, a light source which is capable of emitting the ultraviolet rays, and a light guide member which is capable of transmitting the ultraviolet rays from the light source to the transparent body.

To accomplish other object of the present invention, a cleaning apparatus or a vacuum cleaner in a preferred embodiment of the invention may comprise a motor, a fan, a dust keeping means (dust bag or dust case), a cleaning head having a transparent body capable of transmitting ultraviolet rays, a light source capable of emitting said sheath and a light guide member capable of transmitting the ultraviolet rays from the light source to the transparent body.

Therefore, in case the cleaning head is approaching, contacting or sweeping to the cleaned substance, the dirty components contacted or sticked on the surface of the cleaned substance can be sterilized, dissolved to be cleaned up according to radiation of the ultraviolet rays.

BRIEF DESCRIPTION OF THE DRAWINGS

A complete understanding of the invention may be obtained from the following explanations, in connection with the accompanying drawings; in which.

DESCRIPTION OF THE PREFERRED EMBODIMENTS

Figure 1:
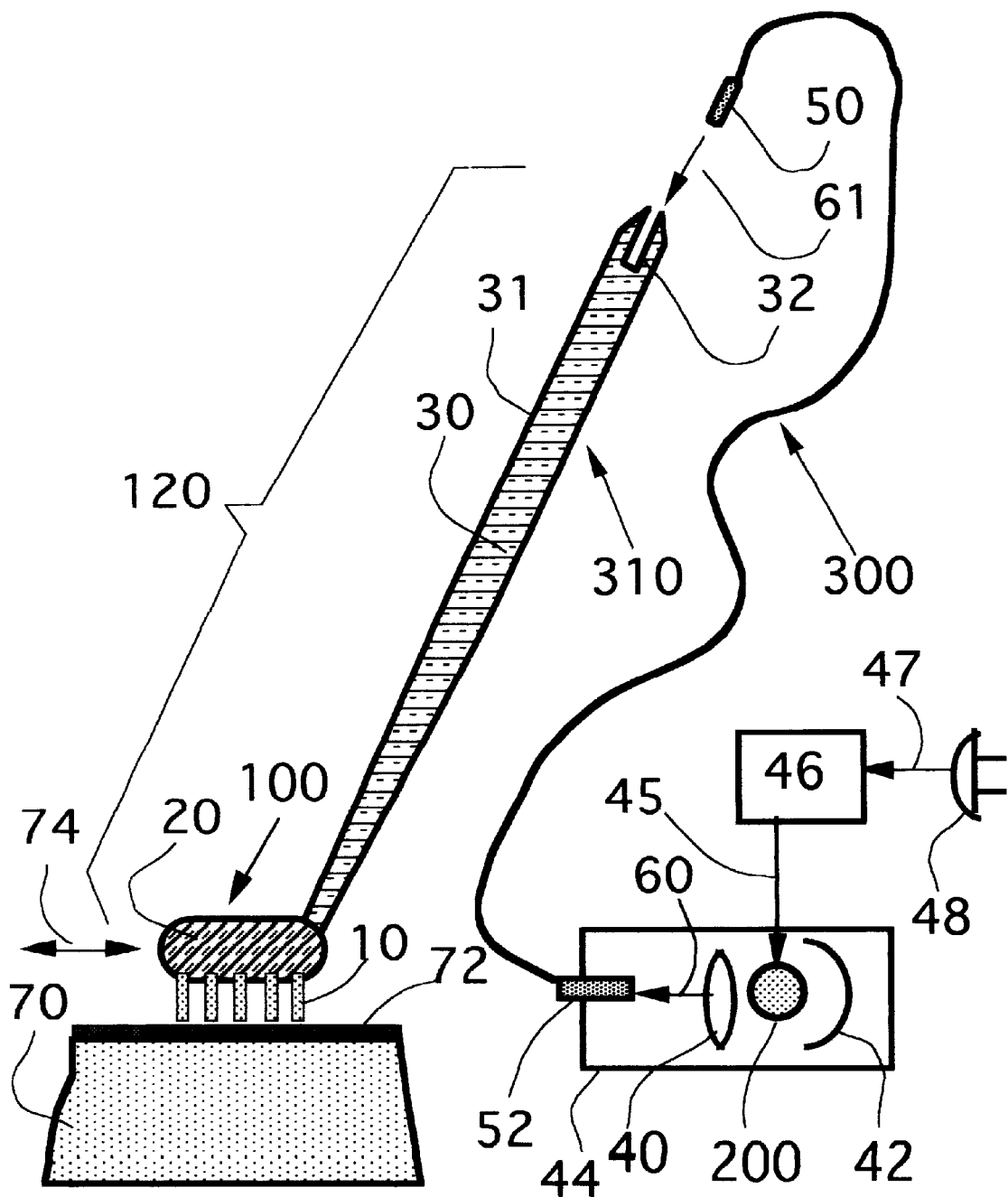
FIG. 1 illustrates a conceptional cross-sectional view of a cleaning apparatus, explaining first preferred embodiment of the present invention.

The present invention will now be described in detail with reference to the drawings.

In the drawings, a relative dimension or size of each part or portion may be shown as somewhat different one to clarify an explanation of the present invention and the same parts or portions have the same reference numerals.

Embodiment No. 1

Reference is made to FIG. 1, FIG. 2, FIG. 3, FIG. 4 and FIG. 5 showing first preferred embodiment of the present invention.

Figure 2:
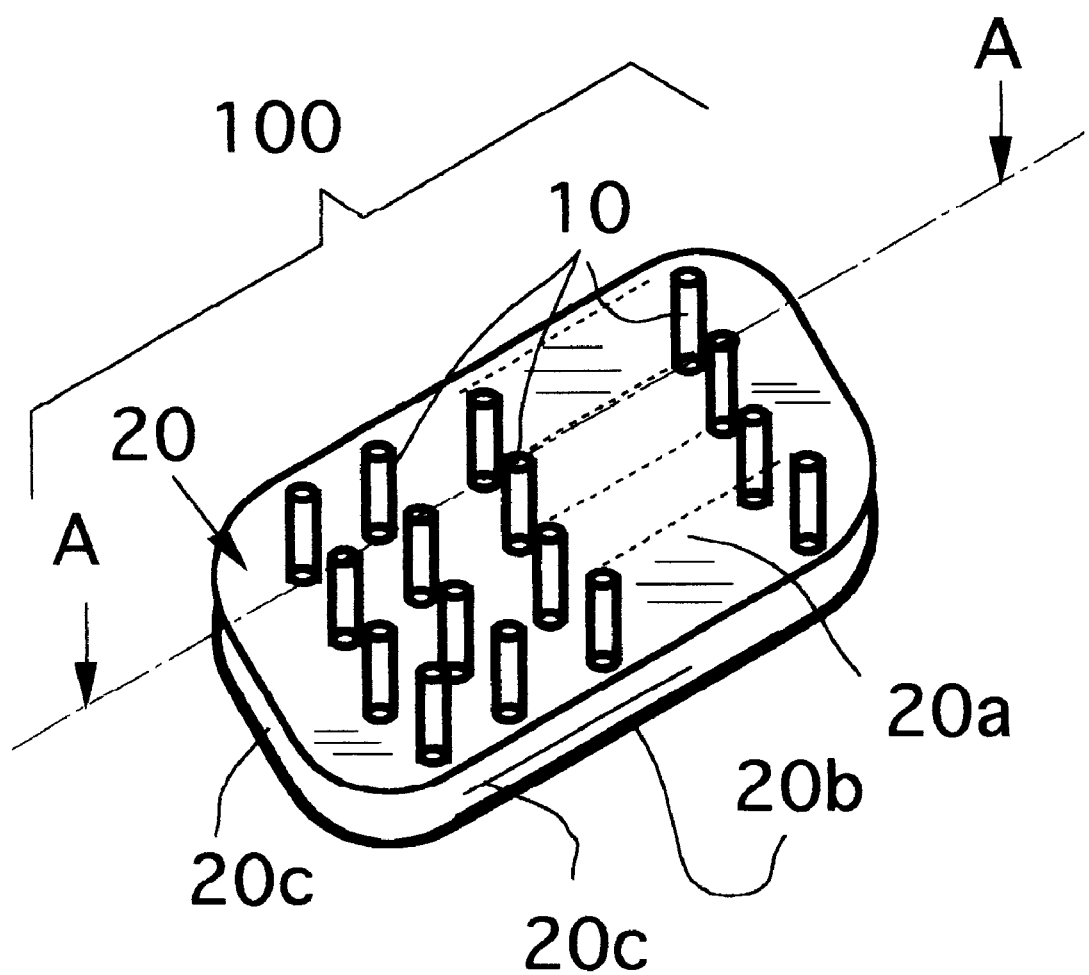
FIG. 2 illustrates a schematic enlarged perspective view of a cleaning head 100 in a cleaning tool 120, explaining first preferred embodiment of the present invention.
Figure 3:
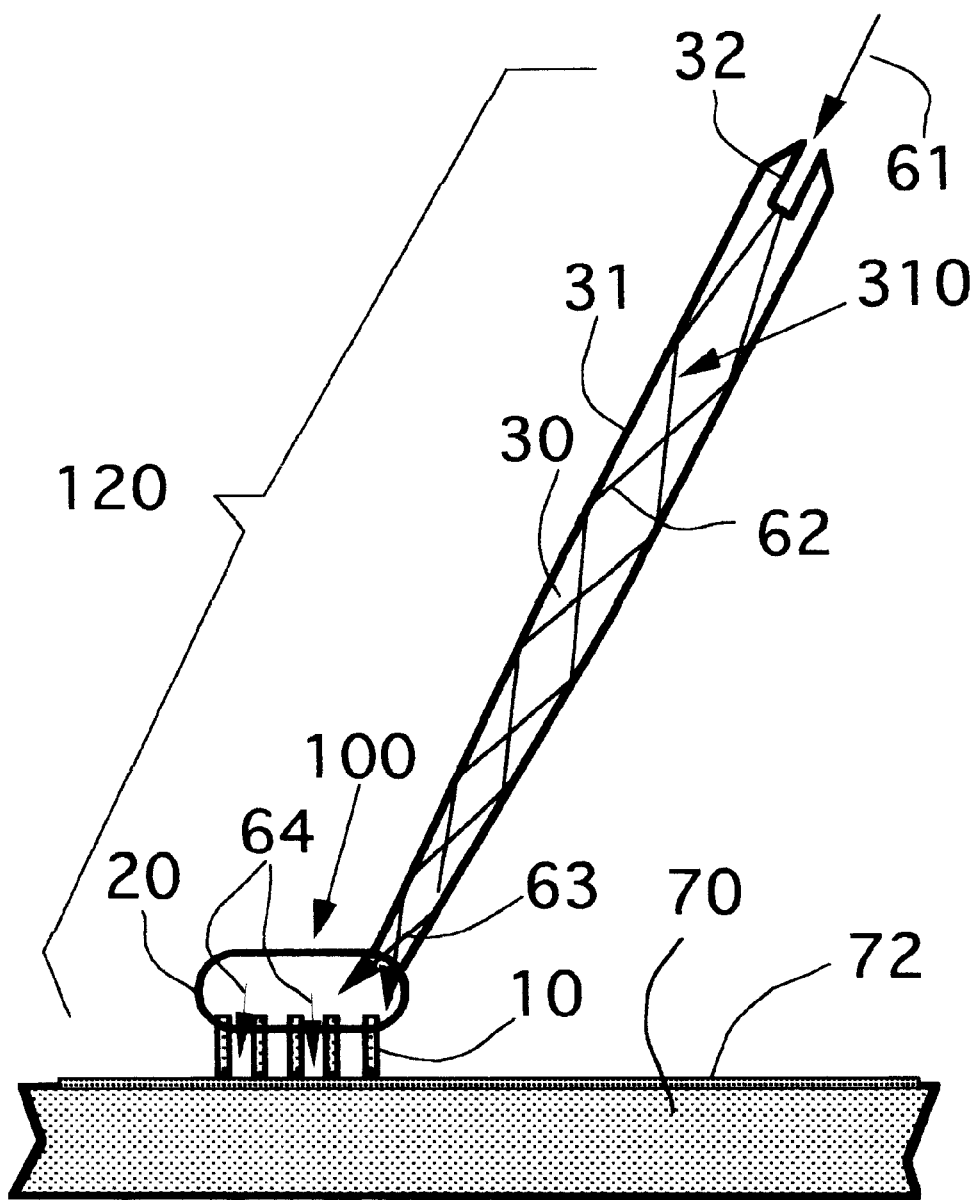
FIG. 3 illustrates a conceptional view of a light transmission passage way in cross-section of the cleaning tool 120 as shown in FIG. 1, explaining first preferred embodiment of the present invention.
Figure 4:
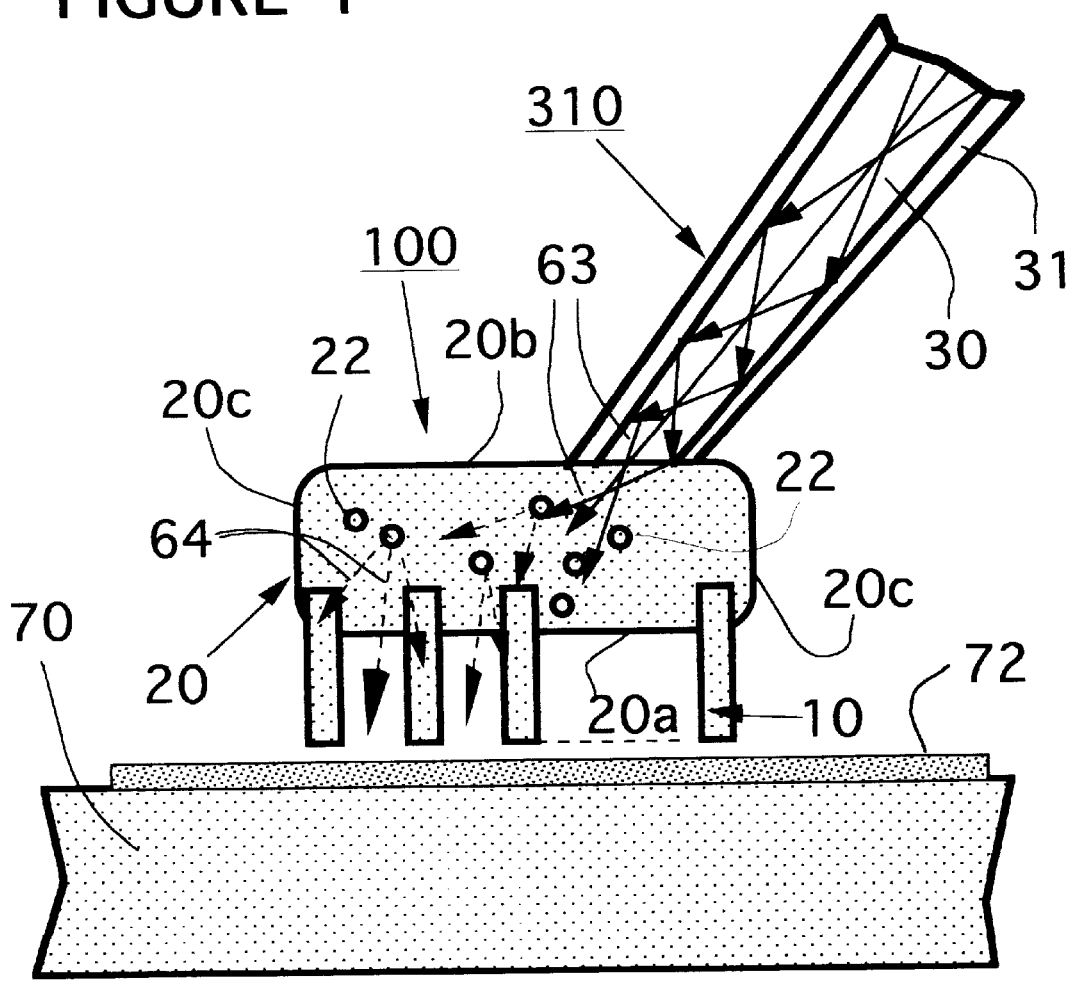
FIG. 4 illustrates a conceptional, partially omitted, enlarged cross-sectional view of the cleaning tool 120 in which a light transmission passage ways are indicated, explaining first preferred embodiment of the present invention.
Figure 5:
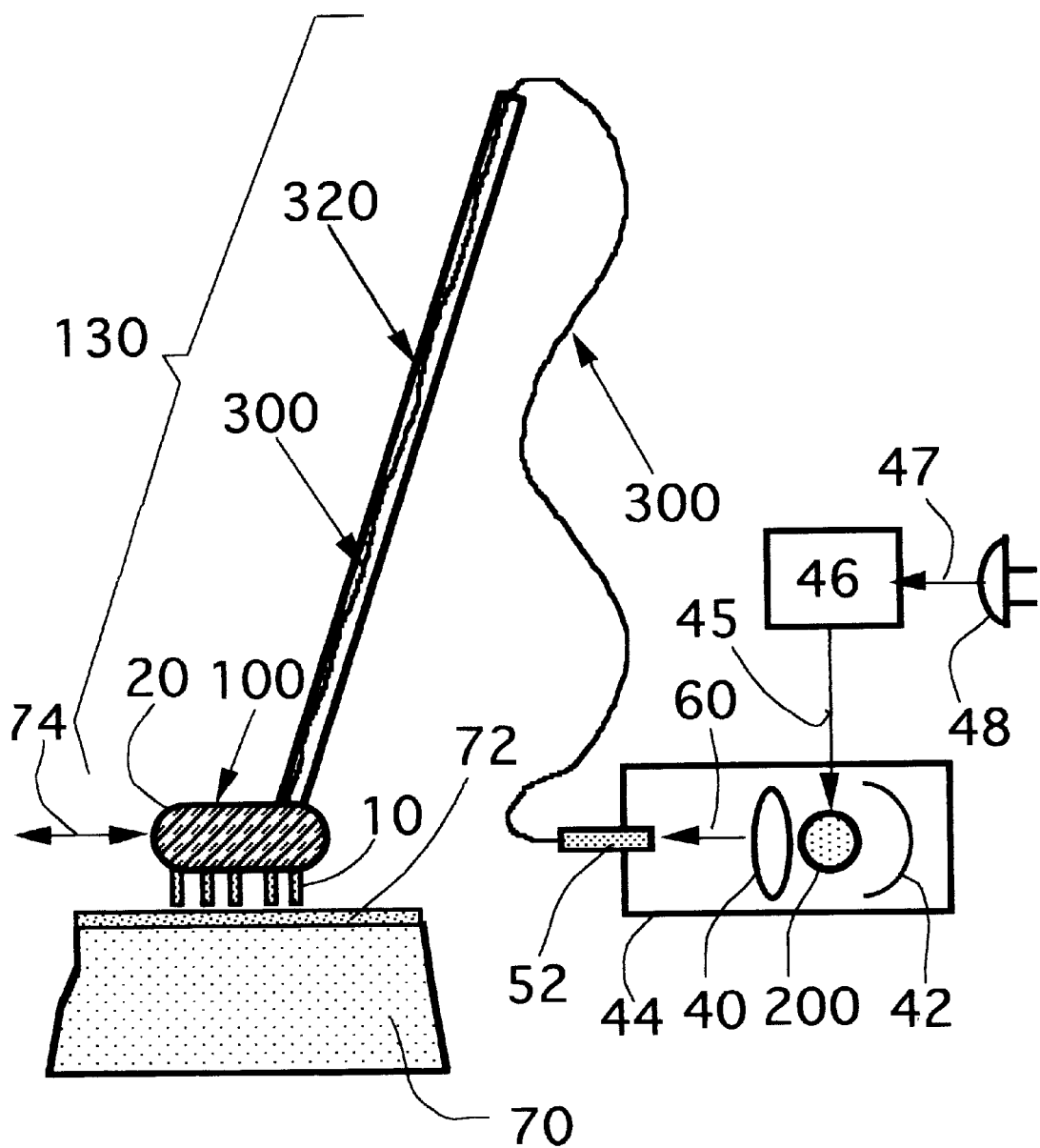
FIG. 5 illustrates a conceptional cross-sectional view of a cleaning apparatus, explaining second preferred embodiment of the present invention.

FIG. 1 shows a conceptional cross-sectional view of a cleaning apparatus. FIG. 2 shows a schematic enlarged perspective view of a cleaning head 100 in a cleaning tool 120. FIG. 3 shows a conceptional view of a light transmission passageway in cross-section of the cleaning tool 120 as shown in FIG. 2. FIG. 4 shows a conceptional partially omitted enlarged cross-sectional view of the cleaning tool 120 in which light transmission passageway is indicated with arrow marks. And FIG. 5 shows an enlarged cross-sectional view of a piece of brush among a group of brushes 10 in the cleaning head 100.

In FIG. 1, FIG. 2, FIG. 3 and FIG. 4, the cleaning apparatus (or cleaning device) 120 is roughly composed of a cleaning tool 120, a light source 200 and an optical fiber or an optical fiber cable 300. The cleaning tool 120 is further composed of a cleaning head 100 and handle 310 with rod like shape extending from the cleaning head 100.

The cleaning head 100 is further composed of a group of multiple brushes 10 and a transparent body 20 in order to fix ends of the brushes 10 and support them in which the transparent body 20 is made of transparent material capable of transmitting the UV rays.

The handle 310 is provided with a light inlet 32 (as shown in FIG. 2 and FIG. 3) which may be a hole, etc. in the most distant terminal of the handle 310 from the cleaning head 100.

As shown in FIG. 4, the handle 310 may be composed of a transparent rod 30 with high refractive index and a transparent sheath 31 with low refractive index, in which both of them 30 and 31 are capable of transmitting the UV rays. The transparent rod 30 may be coated or covered with the transparent sheath 31 around the transparent rod 30. The transparent rod 30 is equivalent to a "core" of an optical fiber having a transparent core and a transparent cladding in which both of them 30 and 31 are capable of transmitting the UV rays. The transparent sheath 31 is equivalent to a "cladding" of the optical fiber functionally. Therefore, the handle 310 is able to transmit almost all the light rays effectively within the rod 30 with high transmission factor (or minimum transmission loss) from the light inlet 32 to the cleaning head 100, similar to the optical fiber based on principle of "total reflection".

Alternatively, a light reflective metallic layer such as aluminum or nickel may be used as a substitute for the transparent sheath 31 in order to obtain similar high transmission factor.

Alternatively, the transparent body 20 may include many light diffusing elements (particles) 22 (as shown in FIG. 4) in the transparent material, that is, many light diffusing particles 22 may be embedded in the transparent body 20. Conventional white pigments may be used for the light diffusing particles 22 such as titanium oxide, aluminum, calcium carbonate and barium carbonate in order to give the transparent body 20 a light diffusing characteristics.

Reference numeral 70 indicates the cleaned substance such as floor, carpet and wall in a building or a house, and reference numeral 72 indicates the dirty component which is contacted or sticked on a surface of the cleaned substance 70, as shown in FIG. 2, FIG. 3 and FIG. 4.

The light source 200 emits (generates) short wavelength rays including the UV rays. For the light source 200, a germicidal lamp may be preferably used for a preferred embodiment of the invention. The germicidal lamp is conventional low or high pressure vacuum discharge lamp including mercury in a vacuum tube, using a UV ray-transmissible glass tube such as transparent fused quarts, which emits the UV rays with short wavelength between the range from 250 nm to 280 nm (center wavelength; 253.7 nm) by discharge of mercury.

Referring again to FIG. 1, the light source 200, the focus lens 40 and the reflector 42 which is positioned in rear of the light source 200 are housed in a light box (or a lamp house) 44. A commercial power is supplied from a power consent 48 to a light control circuit device 46 via an electric cable 47. The light control circuit device 46 controls a lighting of the light source 200 via an electric cable 45. An optical fiber 300 may be composed of flexible cord including a single number of optical fiber capable of transmitting the UV light rays and a protective. The optical fiber 300 has a pair of optical fiber connectors 50 and 52 in both terminals. An optical connector 50 of the optical fiber 300 is connected optically with the optical inlet 32 of the handle 310 and another optical connector 52 is connected optically with an optical output of the lamp house 44. UV light rays 60 emitting from the light source 200 are gathered by the focus lens 40 and the reflector 42. And the UV light rays 60 are input at the optical connector 52 of the optical fiber 300. The UV light rays 60 incident to the optical connector 52 are transmitting inside the optical fiber 300 to the optical connector 50. The UV light rays 60 are going out from the optical connector 50 and become UV light rays 61. The UV light rays 61 are introduced into the transparent 310 via the optical inlet 32 and are transmitting inside the transmitting rod 30 toward the cleaning head 100.

For transmissible materials of the UV rays for the optical fiber 300 (having a core and a cladding), the handle 310 (the rod 30 optically equivalent to the core and the sheath 31 optically equivalent to the cladding) and the transparent body 20 (optically equivalent to the core), such transparent inorganic materials may be used as Fused Quarts (including more than 99.9 weight % of $SiO_2$), Sapphire, Borosilicate glass (composing $SiO_2$; 75.3, $B_2O_3$; 13.8; ZnO, 1.4, $Al_2O_3$; 4.3, NaO; 5.0 weight %), etc. Instead of inorganic materials, such transparent organic materials may be used as Acrylic base resin such as Polymethyl methacrylate (PMMA) (refractive index; $N\approx1.49$), Polycarbonate (PC) ($N\approx1.59$) resin, Polyethylene base resin such as Polyethylene terephthalate (PETP) ($N\approx1.58$), Polystyrene (PS) ($N\approx1.59$) and Fluoride base resin such as Polytetra fluoroethylene (PTFE), ($N\approx1.35$), Epoxy resin (EP) ($N\approx1.55-1.61$), etc. It is noted that the core of the optical fiber 300 (or the equivalent members 30 and 20) must be selected from material with comparatively high refractive index, while the cladding of the optical fiber 300 (or the equivalent members 31) must be selected from material with comparatively low refractive index.

The UV transmissible optical fiber 300 has been put into market. Such optical fiber capable of transmitting the short wavelength rays in ultra violet region is available from multiple of cable manufacturers, such as Mitsubishi Cable Industries Ltd., Japan.

Referring again to FIG. 1, FIG. 3 and FIG. 4, because the UV transmissible handle 310 has the UV transmissible rod 30 with high refractive index and the UV transmissible sheath 31 with high refractive index, the UV light rays 61 and 62 are transmitted effectively repeating multiple of reflections inside of the handle to the cleaning head 100. The UV light rays 63 are incident UV light rays in which the UV light rays 61 and 62 are transmitting into the UV transmissible transparent body 20 of the cleaning head 100.

Therefore, as shown in FIG. 2 and FIG. 4, the UV rays 63 incident to the transparent body 20 are going outside from a front surface 20a of the transparent body 20 and radiate or illuminate the dirty component 72 including bacteria, molds, etc. on the cleaned substance 70 on the cleaned substance 70 such as floor, carpet, wall, etc. so that the dirty component 72 is sterilized. Alternatively, the UV rays 63 incident to the transparent body 20 are diffused at the reflective particles 22 to become diffusing (scattering) UV light rays 64 and the diffusing UV light rays 64 are going outside from a front surface 20a of the transparent body 20 and radiate or illuminate the dirty component 72 on the cleaned substance 70.

A rear surface 20b and a side surface 20c of the transparent body 20 excluding the front surface 20a may be preferably coated with light transmissible layer with low refractive index or light reflecting metallic layer in order to obtain more amount of the UV light output to the dirty component 72.

The brush 10 may preferably have a light reflecting characteristics to reflect the UV rays in which each brush may be composed of a core of organic plastic resin or rubber and light reflective particles (or pigments) such as titanium oxide, aluminum, calcium carbonate and barium carbonate embedded in the core, in which the light reflective particles are exposed in the surface of the core as much as possible. Alternatively, each brush 10 may be composed of a core of organic plastic resin, rubber and metal light and a light reflecting sheath such as organic plastic resin or rubber embedding the light reflecting particles (or pigments) as mentioned above. In another alternative, metallic wire brush may be used such as steel wire with light reflecting metal coating, stainless steel wire, etc.

In all embodiments of the present invention, the same part or the same member has the same reference numeral. Therefore, in explaining various embodiments to be described below, different portions from portions already described in the embodiment NO. 1 are mainly explained and the portions already described are omitted as much as possible due to simplification of explanation.

Embodiment No. 2

FIG. 5 shows second preferred embodiment of the present invention, in which a cleaning apparatus is roughly composed of a cleaning tool 130, a light source 200, a light control circuit device 46 and an optical fiber 300.

The cleaning tool 130 is further composed of a cleaning head 100 and a handle 320. The handle 320 is formed as a pipe of hollow tube, which is connected with the cleaning head 100. The cleaning head 100 is further composed of a group of brushes 10 and a transparent body 20 by which the brushes 10 is fixed (supported).

In the embodiment NO. 2, one terminal of the optical fiber 300 is connected to the cleaning head 100 via an optical fiber connector. A part of the optical fiber 300 is accommodated inside the handle of tube 320 and a rest part is going outside the handle 320. The rest part of the optical fiber 300 is finally connected optically to a light output part of a lamp house 44 via a detachable optical connector 52 of the optical fiber 300.

UV light rays 60 emitting from a light source 200 are gathered by a focus lens 40 and a reflector 42, they are input to the optical fiber 300 through the optical connector 52 and they arrive in the cleaning head 100 through the optical fiber 300.

Therefore, the UV rays 60 incident to the transparent body 20 are finally going outside from a front surface of the transparent body 20 and radiate the dirty component 72 including bacteria, molds, etc. on the cleaned substance 70 such as floor, carpet, wall etc.

In this embodiment NO. 2, an efficient light transmission is employed with minimum transmission loss between the UV light source 200 and the UV transmissible transparent body 20, due to use of the UV transmissible optical fiber 300.

Embodiment No. 3

Figure 6:
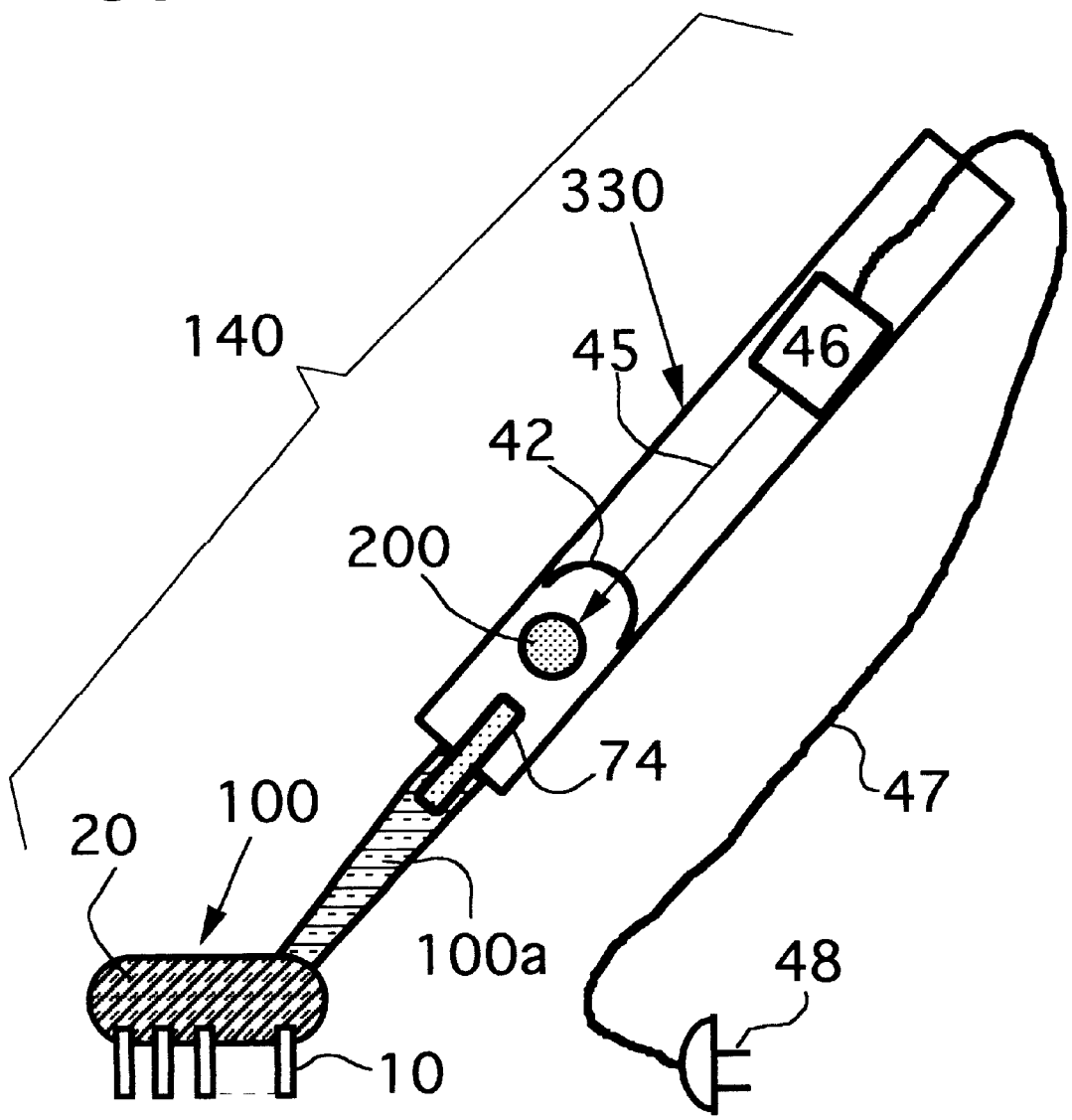
FIG. 6 illustrates a conceptional cross-sectional view of a cleaning apparatus, explaining third preferred embodiment of the present invention.

FIG. 6 shows third preferred embodiment of the present invention, in which a cleaning apparatus is roughly composed of a cleaning tool 140, a light source 200 and a light control circuit device 46. The cleaning tool 140 is further composed of a cleaning head 100, a transparent neck 100a of a part of the cleaning head 100 and a handle 330. The handle 330 is formed as a pipe of hollow tube, which is connected to a terminal of the transparent neck 100a, which is enlarged as taper shape in cross-section toward the handle 330. The cleaning head 100 is further composed of a group of brushes 10 and a transparent body 20 by which the brushes 10 are fixed. The transparent neck 100a is extending with some inclined angle from the cleaning.

In the embodiment NO. 3, the cleaning tool 140, a light source 200, a light control circuit device 46 and a reflector 42 are housed in a hollow portion of the handle 330. Light rays emitting from the light source 200 are optically connected and mechanically fixed with the transparent neck 100a via an optical connector 74.

The light control circuit device 46 is electrically connected with an electric wiring 47, an electric power supply is fed to the light control circuit device 46 via a power consent 48 and the light source 200 is lit on by an power output of the light control circuit device 46. UV light rays emitting from the light source 200 are gathered by the reflector 42 and introduced into a transparent body of the cleaning head 100 through the optical connector 74 and the transparent neck 100a.

Therefore, the UV rays incident to the transparent body 20 are going outside from a front surface of the transparent body 20 and radiate or illuminate the dirty component including such as bacteria, molds etc. on the cleaned substance 70 such as floor, carpet, wall etc.

In the embodiment NO. 3, the cleaning apparatus becomes very compact, because al most all components of the cleaning apparatus are accommodated in the cleaning tool 140.

Embodiment No. 4

Figure 7:
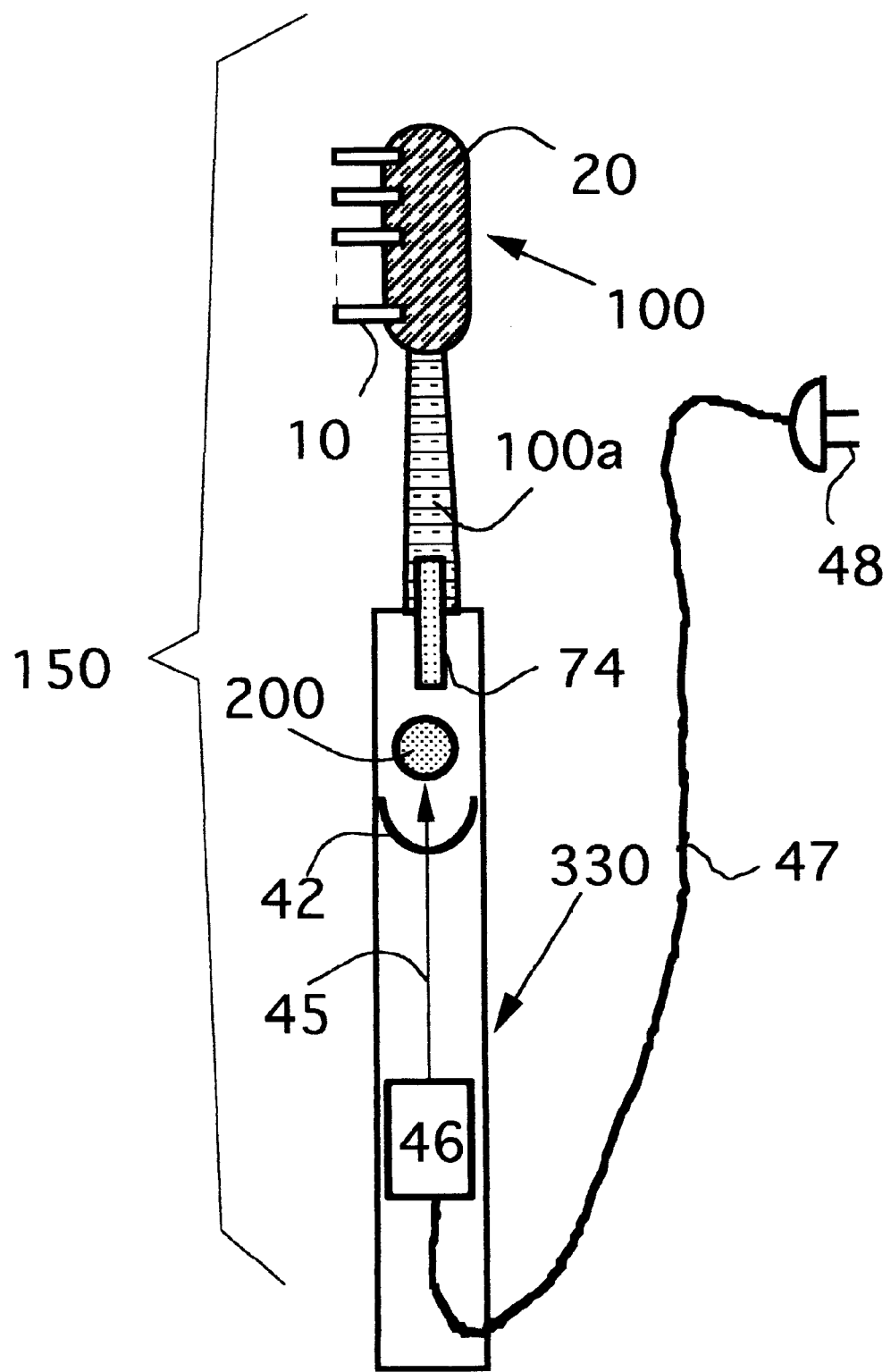
FIG. 7 illustrates a conceptional cross-sectional view of a cleaning apparatus 150, explaining fourth preferred embodiment of the present invention.
Figure 8:
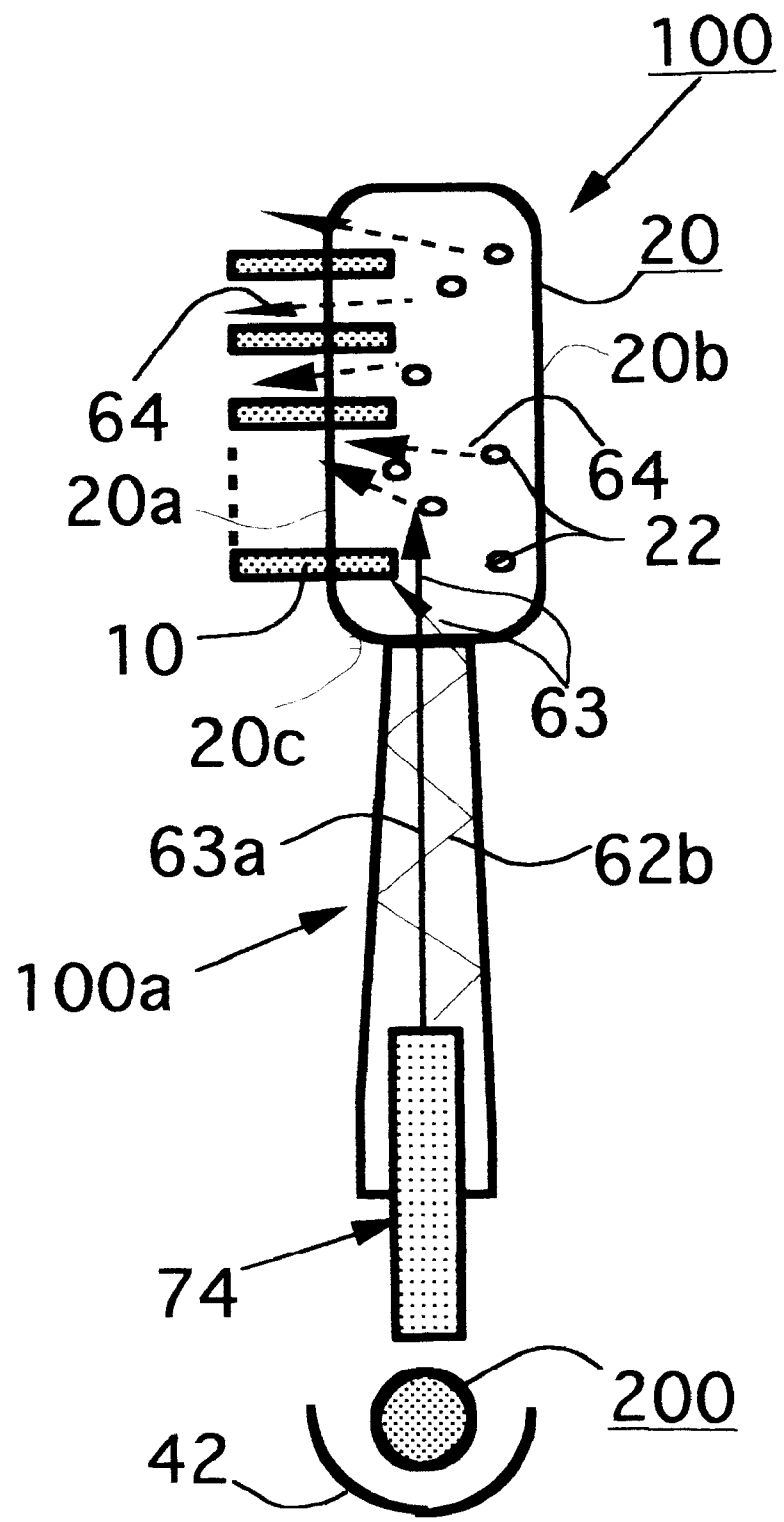
FIG. 8 illustrates a conceptional, partially omitted, enlarged cross-sectional view of the cleaning apparatus 150 in which light transmission passage ways are indicated, explaining fourth preferred embodiment of the present invention.

FIG. 7 and FIG. 8 show fourth preferred embodiment of the present invention. A cleaning apparatus is roughly composed of a cleaning tool 150, a light source 200 and a light control circuit device 46, similar to the embodiment NO. 3. The cleaning tool 150 is further composed of a cleaning head 100, a transparent neck 100a of a part of the cleaning head 100 and a handle 330. The transparent neck 100a is extending vertically from the side surface 20c of the transparent brush supporter 20. The handle 330 is formed as a pipe of hollow tube in which the light source 200, the light control circuit device 46, an electric wiring 45 to connect the light control circuit device 46 and the light source 200, and a reflector 42 are accommodated inside the hollow tube. UV light rays generating from the light source 200 are collected by a reflector 42 at an optical connector 74. And they are incident to the transparent neck 100a of taper shape via the optical connector 74. The light rays 62a arrived at the transparent neck 100a are transmitting directly to the brush supporter 20 of the cleaning head 100 and they 62b are transmitting by repeating multiple reflections to the transparent brush supporter 20. The UV light rays 63 Incident into the brush supporter 20 are striking to many light diffusing particles 22 embedded in the brush supporter 20 and becomes diffusing light rays 64.

Therefore, the UV rays 63 incident to the transparent body 20 are going outside from a front surface 20a of the transparent supporter 20 and radiate dirty components including bacteria, molds, etc. on the cleaned substance.

Therefore, the UV rays incident to the transparent body 20 are going outside from a front surface of the transparent body 20 and radiate or illuminate the dirty component including such as bacteria, molds etc. on the cleaned substance.

In the embodiment NO. 3, the cleaning apparatus becomes very compact, because almost all components of the cleaning apparatus are accommodated in the cleaning tool 150.

Embodiment No. 5

Figure 9:
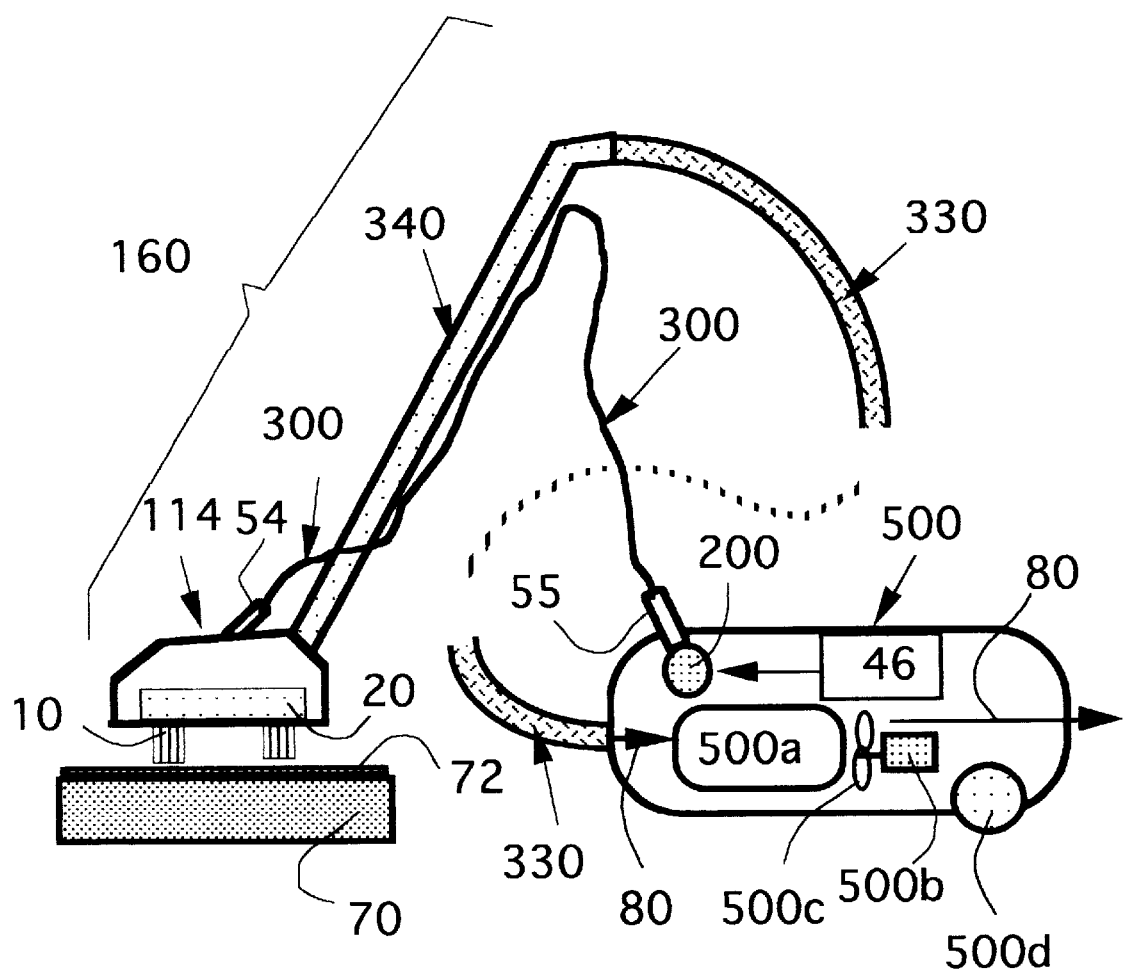
FIG. 9 illustrates a conceptional cross-sectional view of a cleaning apparatus, explaining fifth preferred embodiment of the present invention, in which the invention is applied to a vacuum cleaner.
Figure 10:
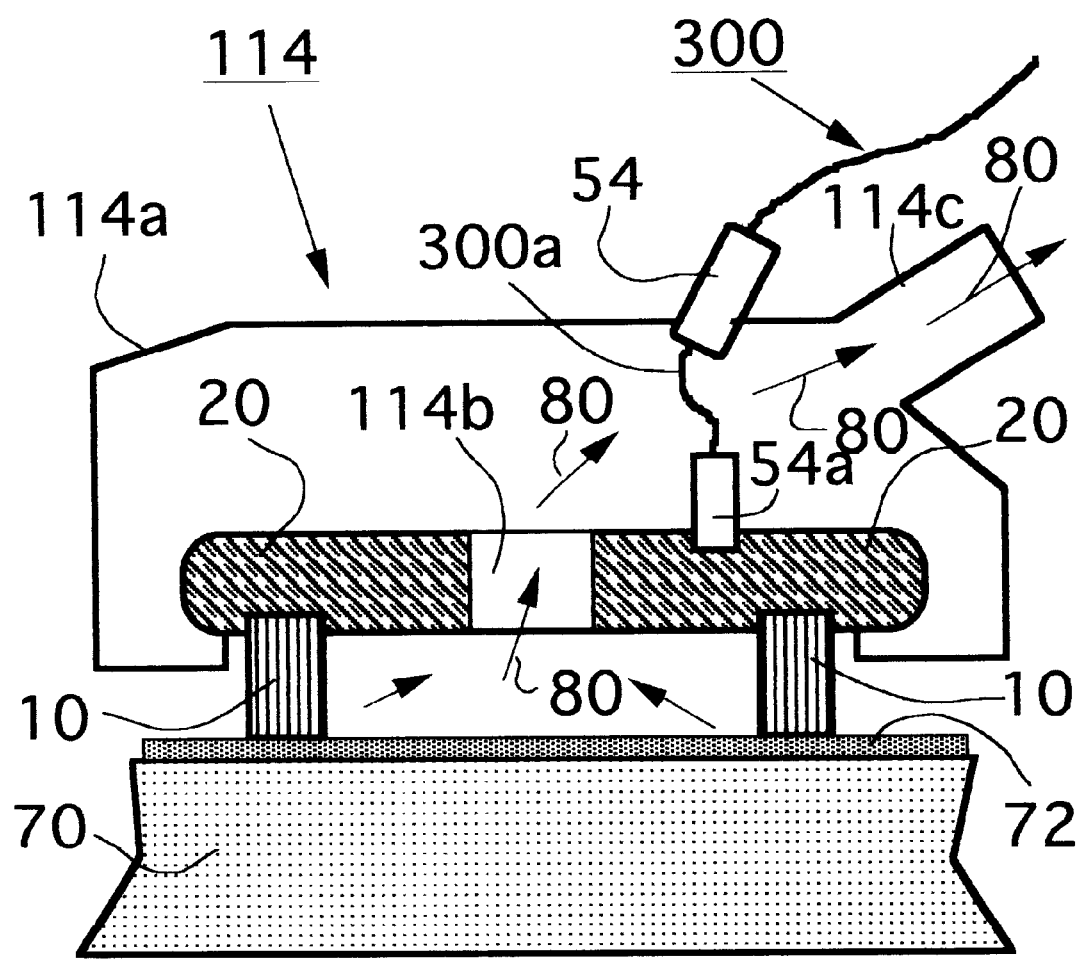
FIG. 10 illustrates a schematic, partially omitted, enlarged cross-sectional view of neighborhood of a cleaning head 114 as shown in FIG. 9, explaining fifth preferred embodiment of the present invention.

Referring to FIG. 9 and FIG. 10, fifth preferred embodiment of the invention is explained in which a cleaning apparatus of the invention is applied to a vacuum cleaner.

As shown in FIG. 9, the vacuum cleaner is roughly comprised of a cleaning tool 160, a cleaner body 500, a flexible hose 330 and an optical fiber cable (or optical fiber) 300. The cleaning tool 160 is further composed of a cleaning head (or nozzle, hood, suction inlet) 114 and a tube type handle (or wand) 340. The cleaner body 500 is further comprised of a motor 500b, a fan 500c rotating by the motor 500b, a dust keeping means (dust bag or dust case) 500a, a light source 200 to emit UV rays, a light control circuit device 46 and wheels (or casters) 500d to move easily on a cleaned substance such as floor and carpet. The cleaning head 114 is further composed of a transparent body 20, a group of brushes 10 and a casing 114a or a hood. The flexible hose 330 is connected to a terminal of the handle 340 in a terminal of the hose 330 and a vacuum inlet of the cleaner body 500 in another terminal of the hose 330.

The optical fiber cable 300 capable of transmitting the UV rays is connected optically with the light source 200 via an optical connector 55 at a terminal of the optical fiber cable 300 and the cleaning head 114 via another optical connector 54 at another terminal of the optical fiber cable 300. Accordingly, the UV rays emitted from the light source 200 housed in the cleaner body 500 is transmitted to the transparent body 20 housed in the cleaning head 114 via the optical fiber cable 300 and radiate the dirty component 72 on the cleaned substance 70.

Therefore, when the fan 500c is rotating according to rotation of the motor 500b, an air pressure in a forward of the fan 500c is decreased and the dirty component 72 on the floor, the carpet, etc. is forced to suck together with an air from the cleaning head 114 and the dirty component 72 is gathered inside the dust bag or dust case 500a through the hollow of the handle 340, the flexible hose 330.

In FIG. 10 showing an enlarged detail of the cleaning head 114, the cleaning head 114 is comprised of a head case 114a, a transparent body 20 having a group of brushes 10 and an air suction hole 114b, a connecting pipe 114c to connect the handle 340, a detachable optical connector 54a to connect optically between the transparent body 20 and an optical fiber 300a. The cleaning head 114 accommodates the transparent body 20 with brushes 10 in the head case 114a and it is constructed to keep air tightness, when the brushes 10 contact or approach to the floor 70 (or carpet etc.). The brushes 10 are fixed in a bottom of the transparent body 20.

Referring again to FIG. 9 and FIG. 10, the optical fiber cable 300 extended from the optical fiber connector 55 in one end is connected to the optical fiber connector 54 in another end fixed at the head case 114. The short optical fiber 300a is optically connected between the optical fiber connector 54 and the optical fiber connector 54a.

Therefore, the dirty component 72 contacted or sticked on the surface of the cleaned substance 70, for an example, the floor are forced to remove from the surface by contacting (or sweeping, brushing) of the brushes 10 and moves to upper portion of the head case 114a via the suction inlet 114b of the transparent body 20 and goes out from the connecting pipe 114c according to an air flow (see arrow 80).

The UV rays transmitted in the cleaning head 114 are further transmitted to the transparent body 20 and radiate the floor 70 etc. so that the dirty component 72 is sterilized.

It is to be understood that the forgoing description is preferred embodiments of the invention and that various changes, modifications, combinations, or equivalents may be made in the invention without departing from the spirit and the scope of the present invention and the appended claims.

What is claimed is:

1. A cleaning apparatus using ultraviolet rays comprising:
    (a) a cleaning head, having a substantially transparent body capable of ultraviolet rays, a first major surface, a second major surface and a side surface;
    (b) a light source, capable of emitting said ultraviolet rays so as to sterilize a substance or substances to be cleaned by irradiation of said ultraviolet rays;
    (c) a light guide member, capable of transmitting said ultraviolet rays from said light source to said transparent body; and
    (d) a light reflecting means composed of at least one light transmissible layer having a lower refractive index than said transparent body or light reflective metal, and being disposed on one major surface of said first major surface and said second major surface, or on said major surface and said side surface.

2. The cleaning apparatus according to claim 1, wherein said light guide member includes a transparent rod and a sheath covered on said transparent rod, wherein said sheath is made of transparent material with lower refractive index than that of said transparent rod.

3. The cleaning apparatus according to claim 1, wherein said light guide member includes a transparent rod and a sheath covered on said transparent rod, wherein said sheath is made of light reflective metal.

4. The cleaning apparatus according to claim 1, wherein said light guide member includes an optical fiber having a transparent core with high refractive index and a transparent sheath with low refractive index, wherein said core and said sheath are capable of transmitting said ultraviolet rays.

5. The cleaning apparatus according to claim 1:
wherein multiple of light diffusing particles are embedded in said transparent body by which said ultraviolet rays incident to said transparent body are diffused.

6. The cleaning apparatus according to claim 1, wherein said transparent body of said cleaning head is made of a transparent organic plastic material which is selected the group consisting of Acrylic resin, Polycarbonate resin, Polyethylene resin, Polystyrene resin, Fluoride resin and Epoxy resin.

7. The cleaning apparatus according to claim 1, wherein said transparent body of said cleaning head is of made of a transparent inorganic material, which is selected the group consisting of Fused quarts, Sapphire and Borosilicate glass.

8. A cleaning apparatus using ultraviolet rays comprising:
(a) a cleaning head, having a transparent body capable of transmitting ultraviolet rays, a first major surface, a second major surface and a side surface;
(b) a light source, capable of emitting said ultraviolet rays so as to sterilize a substance or substances to be cleaned by irradiation of said ultraviolet rays
(c) a light guide member, capable of transmitting said ultraviolet rays from said light source to said transparent body;
(d) a plurality of brush bristles disposed on/in said first major surface and/or said second major surface; and
(e) said brush bristles having light reflecting means for reflecting said ultraviolet rays.

9. The cleaning apparatus according to claim 8, wherein said light guide member includes a transparent rod and a sheath covered on said transparent rod, wherein said sheath is made of transparent material with lower refractive index than that of said transparent rod.

10. The cleaning apparatus according to claim 8:
wherein each of said brush bristles is composed of a core made of resin or rubber and a plurality of light reflecting particles embedded in said core; and
wherein said light reflecting particles are acting as said light reflecting means.

11. The cleaning apparatus according to claim 8:
wherein each of said brush bristles is composed of a core made of resin or rubber and a light reflecting sheath to cover said core; and
wherein said light reflecting sheath is acting as said light reflecting means.

12. The cleaning apparatus according to claim 8:
wherein each of said brush bristles is composed of a metallic wire-like light reflecting member having a light reflecting metallic wire or a metallic wire coated with a light reflecting metal; and a sheath to cover said core; and
wherein said metallic wire-like light reflecting member is acting as said light reflecting means.

13. The cleaning apparatus according to claim 8, further comprising:
a light reflecting means composed of at least one light transmissible laver having a lower refractive index than said transparent body or light reflective metal, and being disposed on one major surface of said first major surface and said second major surface, or on said major surface and said side surface.

14. The cleaning apparatus according to claim 8, wherein said transparent body of said cleaning head is made of a transparent organic plastic material, which is selected the group consisting of. Acrylic resin, Polycarbonate resin, Polyethylene resin, Polystyrene resin, Fluoride resin and Epoxy resin.

15. The cleaning apparatus according to claim 8, wherein said transparent body of said cleaning head is made of a transparent inorganic material, which is selected the group consisting of Fused quarts, Sapphire and Borosilicate glass.

16. A cleaning apparatus comprising:
(a) a cleaning head, having a substantially transparent body capable of ultraviolet rays, a first major surface, a second major surface and a side surface;
(b) a light source, capable of emitting said ultraviolet rays so as to sterilize a substance or substances to be cleaned by irradiation of said ultraviolet rays;
(c) a light guide member, capable of transmitting said ultraviolet rays from said light source to said transparent body; and
(d) a plurality of light diffusing elements embedded in an interior of said transparent body.

17. The cleaning apparatus according to claim 16, further comprising:
a light reflecting means composed of at least one light transmissible layer having a lower refractive index than said transparent body or light reflective metal, and being disposed on one major surface of said first major surface and said second major surface, or on said major surface and said side surface.

18. The cleaning apparatus according to claim 16:
wherein said light diffusing elements are light diffusing particles selected from the group consisting of titanium oxide, aluminum, calcium carbonate and barium carbonate.

19. The cleaning apparatus according to claim 16, wherein said light guide member includes an optical fiber having a transparent core and a transparent sheath wherein both of the core with high refractive index and the sheath with low refractive index are capable of transmitting said ultraviolet rays.

20. The cleaning apparatus according to claim 16, wherein said transparent body of said cleaning head is of made of a transparent material, which is selected the group consisting of Acrylic resin, Polycarbonate resin, Polyethylene resin, Polystyrene resin, Fluoride resin and Epoxy resin, Fused quarts, Sapphire and Borosilicate glass.

* * * * *